United States Patent
Zoican-Loebick et al.

(10) Patent No.: US 12,419,986 B1
(45) Date of Patent: Sep. 23, 2025

(54) SYSTEM FOR DECONTAMINATION OF A VEHICLE INTERIOR

(71) Applicant: Precision Combustion, Inc., North Haven, CT (US)

(72) Inventors: Codruta Maria Zoican-Loebick, North Haven, CT (US); Christian Junaedi, Cheshire, CT (US); Jeffrey G Weissman, Guilford, CT (US); Subir Roychoudhury, Madison, CT (US); Matthew Steinbroner, Newtown, CT (US)

(73) Assignee: PRECISION COMBUSTION, INC., North Haven, CT (US)

(*) Notice: Subject to any disclaimer, the term of this patent is extended or adjusted under 35 U.S.C. 154(b) by 718 days.

(21) Appl. No.: 17/695,272

(22) Filed: Mar. 15, 2022

Related U.S. Application Data

(60) Provisional application No. 63/162,605, filed on Mar. 18, 2021.

(51) Int. Cl.
  *A61L 9/14* (2006.01)
  *A61L 9/20* (2006.01)
  *B60H 3/06* (2006.01)

(52) U.S. Cl.
  CPC ............ *A61L 9/145* (2013.01); *A61L 9/205* (2013.01); *B60H 3/0608* (2013.01); *A61L 2209/14* (2013.01); *A61L 2209/22* (2013.01); *B60H 2003/0675* (2013.01)

(58) Field of Classification Search
  None
  See application file for complete search history.

(56) References Cited

U.S. PATENT DOCUMENTS

| | | | |
|---|---|---|---|
| 5,051,241 A | 9/1991 | Pfefferle | |
| 6,156,444 A | 12/2000 | Smith | |
| 6,746,557 B2 | 6/2004 | Durand | |
| 7,141,092 B1 | 11/2006 | Roychoudhury | |
| 7,504,047 B2 | 3/2009 | Castaldi | |
| 7,964,023 B2 | 6/2011 | Zhu | |
| 10,464,044 B1 | 11/2019 | Loebick | |
| 10,994,241 B1 | 5/2021 | Junaedi | |
| 11,015,128 B1 | 5/2021 | Loebick | |
| 2010/0143205 A1* | 6/2010 | Engelhard | A61L 9/20 422/121 |
| 2019/0063763 A1* | 2/2019 | Kleinberger | B01D 46/521 |
| 2022/0111350 A1 | 4/2022 | Weissman | |

FOREIGN PATENT DOCUMENTS

| | | | | |
|---|---|---|---|---|
| CN | 111744046 A | * | 10/2020 | ............ A61L 9/205 |

OTHER PUBLICATIONS

Wu, S. CN111744046A-translated document (Year: 2020).*

* cited by examiner

*Primary Examiner* — Jelitza M Perez
(74) *Attorney, Agent, or Firm* — Andrew D. Gathy

(57) ABSTRACT

A decontamination system comprising an enclosure having sidewalls, the sidewalls defining a cavity; an inlet fluidly coupled to the cavity, the inlet configured to receive air into the cavity; an outlet fluidly coupled to the cavity, the outlet configured to discharge the air from the cavity; a bed scrubber located within the cavity fluidly coupled to the inlet and the outlet; the bed scrubber comprising a substrate with decontamination materials attached to the substrate; and a blower fluidly coupled to the inlet and the outlet, the blower configured to transfer air from the inlet through the bed scrubber and out the outlet.

20 Claims, 3 Drawing Sheets

SYSTEM FOR DECONTAMINATION OF A VEHICLE INTERIOR

CROSS-REFERENCE TO RELATED APPLICATIONS

This application claims priority to U.S. Provisional Application No. 63/162,605 filed Mar. 18, 2021.

BACKGROUND

The present disclosure is directed to a system and process for actively decontaminating combat vehicles interior by recirculating cabin air through a sorbent bed having a metal mesh or nano fibers coated with sorbents and catalysts that have antiviral and antibacterial properties.

Exposure to airborne pathogens is a common denominator in affecting the warfighter's health. Infectious diseases have been of great significance to the U.S. military, with acute respiratory infections comprising a large threat. During military deployments, such infections accounted for 14% of all medical encounters, being exceeded only by noncombat orthopedic injuries.

The aerosolized transmission of disease occurs through both droplet and airborne means. Droplet transmission is defined as the transmission of diseases by expelled particles that are likely to settle to a surface quickly, typically within three feet of the source. Thus, for example, in order for an infection to be caused by droplet transmission, a susceptible individual must be close enough to the source of the infection (e.g., an infected individual) in order for the droplet (containing the infectious microorganism) to make contact with the susceptible individual's respiratory tract, eyes, mouth, nasal passages, and so forth. In contrast, airborne transmission is defined as the transmission of infection by expelled particles that are comparatively smaller in size and thus can remain suspended in air for long periods of time. Airborne particles are particularly worrisome simply because they can remain suspended in the air for extended periods of time and can be particularly detrimental in small enclosed spaces where there are no air currents to disperse them.

Although not enough is known about the coronavirus COVID-19(SARS-CoV-2), research appears to suggest that the virus falls into the airborne particles category. Other airborne pathogens that can be easily transmitted in enclosed cabin air include (but not limited to) the influenza virus; Respiratory Syncytial Virus (pneumonia); Paramyxovirus (mumps); *Bordetella pertussis* bacteria (whooping cough); *Haemophilus influenzae* bacteria (meningitis) and *Mycobacterium tuberculosis* bacteria (TBC).

What is needed is a system and process for actively decontaminating the cabin interior of combat vehicles both during deployment (manned) and storage (unmanned) to reduce exposure of military personnel.

SUMMARY

In accordance with the present disclosure, there is provided a decontamination system comprising an enclosure having sidewalls, the sidewalls defining a cavity; an inlet fluidly coupled to the cavity, the inlet configured to receive air into the cavity; an outlet fluidly coupled to the cavity, the outlet configured to discharge the air from the cavity; a bed scrubber located within the cavity fluidly coupled to the inlet and the outlet; the bed scrubber comprising a substrate with decontamination materials attached to the substrate; and a blower fluidly coupled to the inlet and the outlet, the blower configured to transfer air from the inlet through the bed scrubber and out the outlet.

A further embodiment of any of the foregoing embodiments may additionally and/or alternatively include the decontamination materials are configured to deactivate pathogens.

A further embodiment of any of the foregoing embodiments may additionally and/or alternatively include the decontamination materials comprise sorbent or catalyst materials functionalized with particles that have antiviral, antibacterial or antifungal properties.

A further embodiment of any of the foregoing embodiments may additionally and/or alternatively include the substrate comprises at least one of a mesh and a nano fiber support and combinations thereof.

A further embodiment of any of the foregoing embodiments may additionally and/or alternatively include the decontamination system further comprising at least one UV-light source configured to radiate photo-catalysts coupled to the substrate.

A further embodiment of any of the foregoing embodiments may additionally and/or alternatively include the substrate comprises an ultra-short-channel-length metal substrate.

A further embodiment of any of the foregoing embodiments may additionally and/or alternatively include the decontamination system further comprising a power source electrically coupled to the substrate configured to electrically heat the substrate to a predetermined temperature configured to deactivate a pathogen.

In accordance with the present disclosure, there is provided a vehicle equipped with a decontamination system comprising a vehicle comprising a cabin, the cabin defining an interior and an exterior; an enclosure having sidewalls, the sidewalls defining a cavity; an inlet fluidly coupled to the cavity, the inlet configured to receive air into the cavity from at least one of the interior of the cabin and the exterior of the cabin; an outlet fluidly coupled to the cavity, the outlet configured to discharge the air from the cavity into the cabin; a bed scrubber located within the cavity fluidly coupled to the inlet and the outlet; the bed scrubber comprising a substrate with decontamination material attached to the substrate; and a blower fluidly coupled to the inlet and the outlet, the blower configured to transfer the air from the inlet through the bed scrubber and out the outlet.

A further embodiment of any of the foregoing embodiments may additionally and/or alternatively include the decontamination materials comprise sorbent or catalyst material functionalized with particles that have antiviral, antibacterial or antifungal properties.

A further embodiment of any of the foregoing embodiments may additionally and/or alternatively include the substrate comprises layers of at least one of a mesh and a nano fiber support and combinations thereof.

A further embodiment of any of the foregoing embodiments may additionally and/or alternatively include the vehicle equipped with a decontamination system further comprising at least one UV-light source configured to radiate photo-catalysts coupled to the substrate.

A further embodiment of any of the foregoing embodiments may additionally and/or alternatively include the substrate comprises an ultra-short-channel-length metal substrate.

A further embodiment of any of the foregoing embodiments may additionally and/or alternatively include the vehicle equipped with a decontamination system further comprising a power source electrically coupled to the substrate configured to electrically heat the substrate to a predetermined temperature configured to deactivate a pathogen.

In accordance with the present disclosure, there is provided a process for decontamination of a space comprising fluidly coupling the decontamination system to the space, the decontamination system comprising an enclosure having sidewalls, the sidewalls defining a cavity; an inlet fluidly coupled to the cavity, the inlet configured to receive air into the cavity; an outlet fluidly coupled to the cavity, the outlet configured to discharge the air from the cavity into the space; a bed scrubber located within the cavity fluidly coupled to the inlet and the outlet; the bed scrubber comprising a substrate with decontamination material attached to the substrate; and a blower fluidly coupled to the inlet and the outlet, the blower configured to transfer the air from the inlet through the bed scrubber and out the outlet into the space; activating the blower; directing the air through the bed scrubber; contacting the air to the decontamination material; deactivating a pathogen contained in the air; and discharging the air from the outlet into the space.

A further embodiment of any of the foregoing embodiments may additionally and/or alternatively include the decontamination materials comprise sorbent or catalyst materials functionalized with particles that have antiviral, antibacterial or antifungal properties.

A further embodiment of any of the foregoing embodiments may additionally and/or alternatively include the substrate comprises at least one of a mesh and a nano fiber support and combinations thereof.

A further embodiment of any of the foregoing embodiments may additionally and/or alternatively include the substrate comprises an ultra-short-channel-length metal substrate.

A further embodiment of any of the foregoing embodiments may additionally and/or alternatively include the process further comprising illuminating the decontamination material with at least one UV-light source configured to radiate the decontamination materials comprising photocatalysts coupled to the substrate.

A further embodiment of any of the foregoing embodiments may additionally and/or alternatively include the process further comprising electrically heating the substrate to a predetermined temperature configured to deactivate a pathogen with a power source electrically coupled to the substrate.

A further embodiment of any of the foregoing embodiments may additionally and/or alternatively include the space is selected from the group consisting of a vehicle cabin, a ships cabin, and an aircraft cabin, as well as Personal Protective Equipment (PPE).

Other details of the decontamination system and process are set forth in the following detailed description and the accompanying drawings wherein like reference numerals depict like elements.

DETAILED DESCRIPTION

Figure 1:
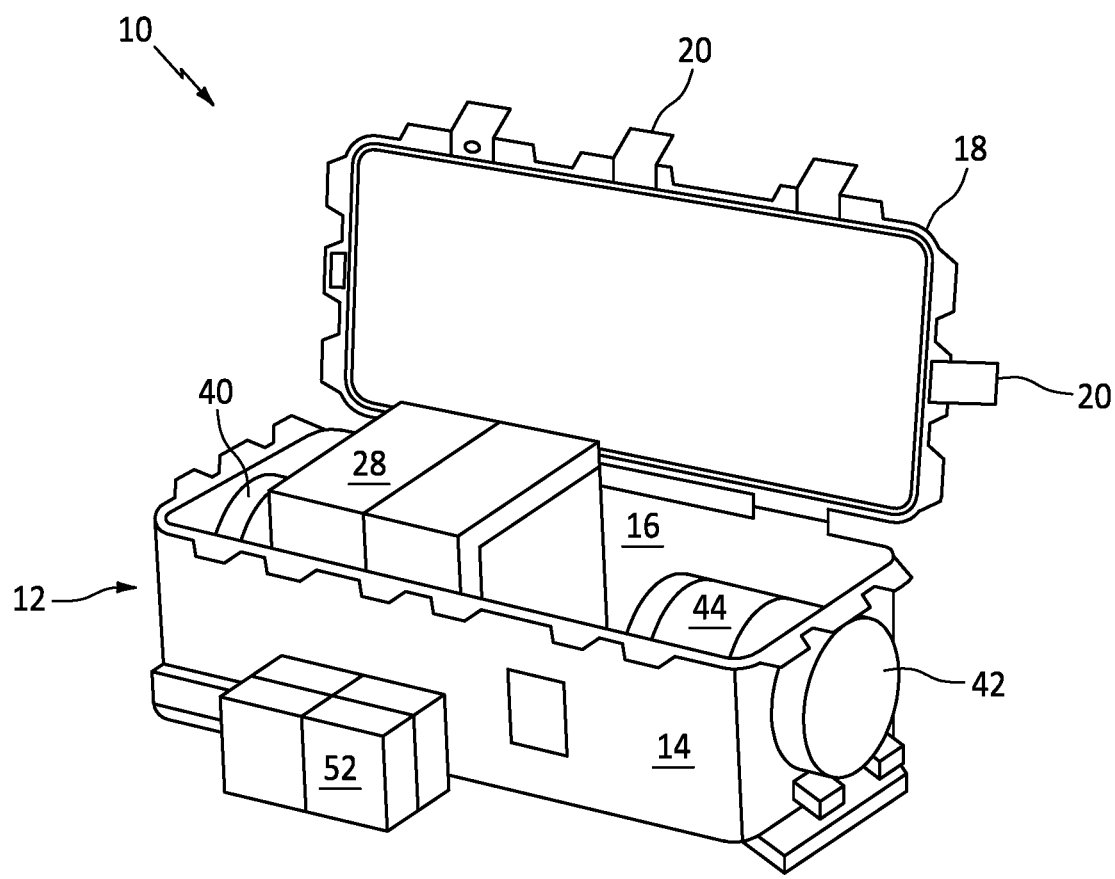
FIG. 1 is an exemplary decontamination system.
Figure 2:
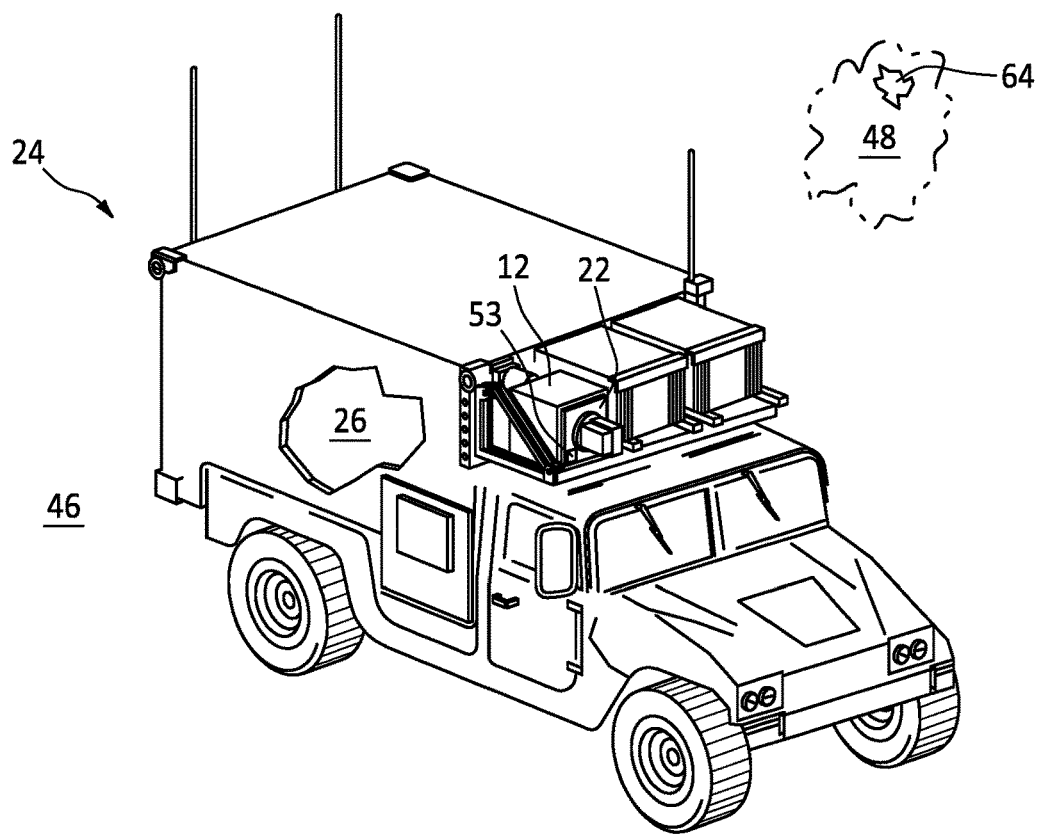
FIG. 2 is an exemplary vehicle equipped with an exemplary decontamination system.

Referring now to FIG. 1 and FIG. 2, an exemplary decontamination system 10 is shown. The decontamination system 10 includes an enclosure 12 having sidewalls 14 forming a cavity 16. The sidewalls 14 can include a removable cover 18 for access to the cavity 16. In an exemplary embodiment, the cover 18 can include latches 20 for latching the cover 18 to the sidewalls 14. In an exemplary embodiment the enclosure 12 can be formed as a rectilinear shape, a tubular shape, a spherical shape and the like. In another exemplary embodiment, the enclosure 12 can be made unitary with a component 22 of a vehicle 24 as shown in FIG. 2. The enclosure 12 can be in fluid communication with an interior or cabin 26 of the vehicle 24.

Figure 3:
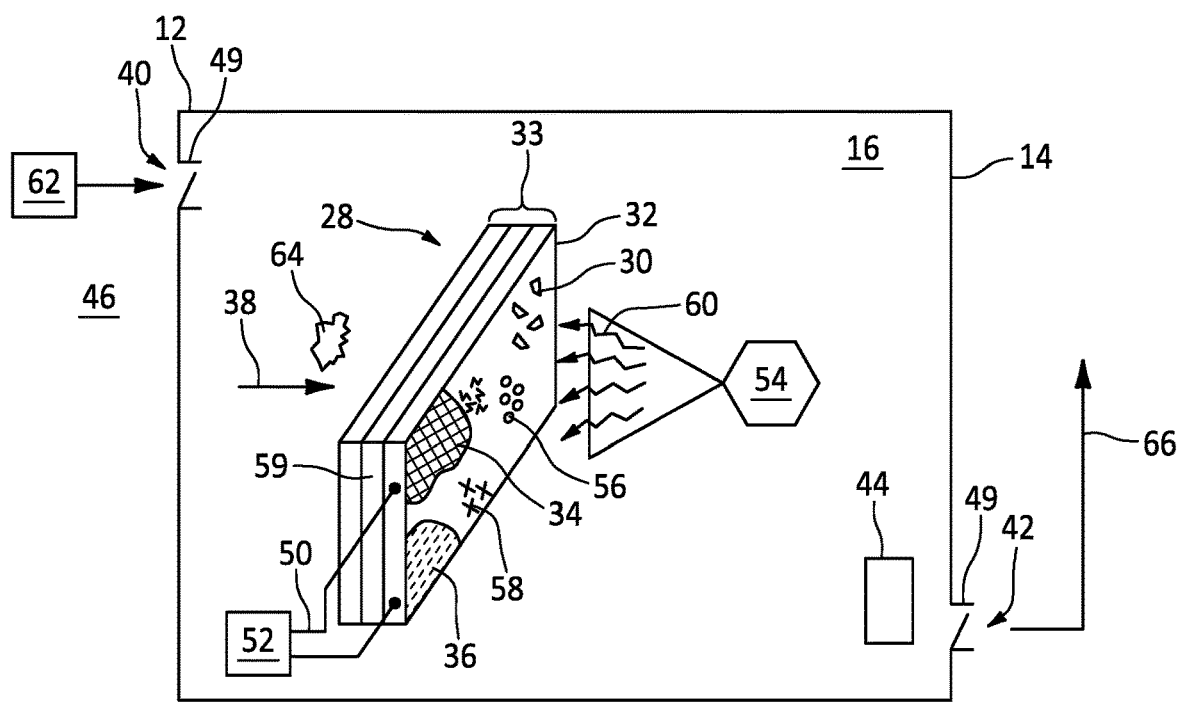
FIG. 3 is a schematic diagram of an exemplary decontamination system.

Referring also to FIG. 3, the enclosure 12 can include a scrubber bed 28 comprising decontamination materials 30 such as sorbents and catalysts coated on a substrate 32. The substrate 32 can be formed in layers 33. The substrate 32 can include a mesh 34 or a nano fiber support 36 or any combination thereof. The mesh elements 34 or fiber support 36 can be deployed horizontally or radially relative a direction of air flow 38 within the enclosure 12.

The decontamination material 30 can include sorbent materials, catalysts and the like with antiviral and antimicrobial properties deposited on an ultra-short-channel-length metal substrate 32. It is understood that any short contact time substrate made of ceramic or metal, such as the MICROLITH® brand substrate 32 can be utilized. The deposition of the decontamination material 30 onto the metal substrate 32 can be implemented by various methods. Alternatively, finished decontamination materials 30 deposited and bound to an ultra-short-channel-length metal substrate 32 can be purchased commercially from Precision Combustion, Inc., North Haven, Connecticut. The metal substrate 32 is preferably employed in a mesh 34 or fiber support 36 form; but the substrate 32 is not limited to such structures, and other structures may be suitable, such as monoliths, fabric, either metals or non-metals and the like.

In another embodiment, the decontamination material 30 comprises one or more sorbent materials, and the like with antiviral and antimicrobial properties, deposited on a MICROLITH® brand ultra-short-channel-length mesh 34 substrate 32. The metal mesh 34 is constructed from any conductive metal or combination of metals provided that the resulting structure is capable of withstanding the temperatures and chemical environment to which it is exposed. Suitable non-limiting materials of construction for the metal mesh 34 include iron-chromium alloys, iron-chromium-aluminum alloys, and iron-chromium-nickel alloys. Such metal meshes 34 are available commercially, for example, from Alpha Aesar and Petro Wire & Steel. The MICROLITH® brand substrate 32 can be obtained commercially from Precision Combustion, Inc., noted hereinabove. A description of the technology can be found, for example, in U.S. Pat. No. 5,051,241, incorporated herein by reference. Generally, the design comprises ultra-short-channel-length, low thermal mass metal monoliths that contrast with prior art monoliths having longer channel lengths. For the purposes of this invention, the term "ultra-short-channel-length" refers to channel lengths in a range from about 25 microns (µm) (0.001 inch) to about 500 µm (0.02 inch). Thus, in visual appearance the preferred metal mesh substrate 32 of ultra-short-channel-length looks like a reticulated net or screen. In contrast, the term "long channels" pertaining to prior art monoliths refers to channel lengths greater than about 5 mm (0.20 inch) upwards of 127 mm (5 inches). (Note that the channel length of the substrate is not to be confused with the length of the catalyst bed. The two lengths are different in kind and degree.)

As compared with prior art monolithic substrates, the preferred MICROLITH® brand ultra-short-channel-length metal mesh substrate facilitates packing more active surface area into a smaller volume and provides increased reactive area for a given pressure drop. Whereas in prior art honeycomb monoliths having conventional long channels, a fully developed boundary layer is present over a considerable length of the channels; in contrast, the ultra-short-channel-length characteristic of the preferred catalyst of this invention avoids boundary layer buildup. Since heat and mass transfer coefficients depend on boundary layer thickness, avoiding boundary layer buildup enhances transport properties. The advantages of employing the ultra-short-channel-length substrate, and preferably, the MICROLITH® brand thereof, to control and limit the development of a boundary layer of a fluid passing there through is described in U.S. Pat. No. 7,504,047, which is a Continuation-In-Part of U.S. Pat. No. 6,746,657 to Castaldi, both patents incorporated herein by reference.

The ultra-short-channel-length metal substrate 32 employed in this invention can be provided in any configuration or structure, provided that the decontamination process of this invention is operable. One alternative configuration comprises a coil (or coiled configuration) in which a sheet of metal mesh 34 is rolled on itself to provide for a radial flow path from an inlet of inner diameter to an outlet of larger outer diameter. Alternatively, the decontamination material 30 can be employed as a sheet as PPE or a plurality of mesh layers 34 stacked, typically, in an orderly-pile one on the other, such as for collective protection. In the stacked bed scrubber 28, the number of layers advantageously ranges from 2 to about 500 or more. The stack of layers 34 is typically compressed to reduce or minimize void spaces between each layer. In the coiled or stack configuration, the plurality of metal mesh layers 33 provides for a plurality of void spaces in random order. For the purposes of this invention, the term "bed scrubber" comprises the entire assembly, e.g., coil or stack, of substrate(s).

More specifically, the MICROLITH® brand metal mesh typically is configured with a plurality of pores having a diameter ranging from about 0.25 millimeters (mm) to about 1.0 mm, with a void space greater than about 60 percent, preferably up to about 80 percent or more. A ratio of channel length to diameter is generally less than about 2:1, preferably less than about 1:1, and more preferably, less than about 0.5:1. Preferably, the ultra-short-channel-length metal mesh 34 has a cell density ranging from about 100 to about 1,000 cells or flow paths per square centimeter. The ultra-short-channel-length metal mesh 34 can be constructed as disclosed, for example, in U.S. Pat. No. 6,156,444, incorporated herein by reference.

In another embodiment, the one or more layers of metal mesh are replaced by a fiber support 36 comprising a three-dimensional interconnected network of solid struts defining a plurality of pores of an open-cell configuration. The pores can have any shape or diameter; but typically, the number of pores that subtend one inch designate a "pore size," which for most purposes ranges from about 5 to about 40 pores per inch. The relative density of such foams, taken as the density of the foam divided by the density of solid parent material of the struts, typically ranges from about 2 to about 15 percent. Fiber supports 36 are commercially available in a variety of alloys capable of withstanding the operating temperatures of the decontamination process of this invention.

The air 38 can be drawn into the enclosure 12 through at least one inlet 40 and discharged out of the enclosure through an outlet 42 and/or recirculated through the enclosure 12 with a blower 44. The outlet 42 can be fluidly coupled to the vehicle interior 26. The inlet 40 can be fluidly coupled to the exterior 46 of the enclosure 12 and/or the vehicle interior 26 and configured to deliver potentially contaminated air 48 to the cavity 16 of the enclosure 12 for contact with the scrubber bed 28. The potentially contaminated air 48 can be located at the exterior 46 and/or the vehicle interior 26. Valves or louvers 49 can be fluidly coupled to the inlet 40 and/or outlet 42 to control the flow of the air 38, 48. It is contemplated that the present disclosure can be extended to all cabin interiors where multiple people have to reside together as a collective protection device such as Navy fleet, aircraft, public transportation, office space and the like or can also be extended to Personal Protective Equipment (PPE).

In an exemplary embodiment, the substrate 32 can be connected to an electrode terminal 50 to allow for resistive heating. The power to resistively heat the substrate 32 can be supplied by power source 52, such as grid power, a battery pack, a solar array or can be connected to the vehicle's electrical system 53 during operation.

In another exemplary embodiment, the substrate 32 of metallic mesh 34 or nano fiber support 36 can be restively heated to temperatures that are known to deactivate pathogens 64. For the novel coronavirus SARS-CoV-2 (COVID-19) for example, the temperature should be a minimum of 56 degrees Centigrade (° C.), and a more preferable a temperature of 70-80° C. to reduce the pathogen 64 deactivation time to under 2 minutes.

In an exemplary embodiment, the enclosure 12 can include at least one UV-light source 54. The UV-light source 54 can be placed inside the interior 16 of the enclosure 12 to activate photo-catalysts 56 coated on the substrate 32 that can effectively remove pathogens 64.

The substrate 32 comprising metallic mesh 34 can be coated with photo-catalysts 56 to deter the spread of viruses by disassembling them on a molecular level. Organic matter reacts with oxygen on the photo-catalyst 56 surface pulling away the electrons from chemical functional bonds that form the components of viruses and bacteria. In an exemplary embodiment, the catalyst 56 can be any catalyst with known photocatalytic activity such as $TiO_2$ or $TiO_2$ promoted with metal oxides and metal nanoparticles, such as ceria, zirconia and platinum. The UV-light source 54 can be a commercially available UV-lamp operating at wavelengths from 315-400 nm for UV-A, 100-280 nm for UV-C, or more broadly to include deep UV-C and near visible blue, from about 50 nm to about 450 nm.

The decontamination material 30 inside the bed scrubber 28 can include sorbent materials coated with functionalities that have antiviral, antibacterial or antifungal properties. In an exemplary embodiment the sorbent materials 58 can include silver, zinc, or copper nanoparticles either coated directly on the substrate 32 or the sorbent materials 58 can include metal nanoparticles coated directly on the substrate 32 or chemically reacted with graphene, graphene oxide, alumina, activated carbon or silica to form functionalized active materials followed by coating on the substrate 32. In another exemplary embodiment, silver, copper or zinc nanoparticles have proven antimicrobial potential against bacteria, but have also proven to be active against several types of viruses including hepatitis B virus, herpes simplex virus, and respiratory syncytial virus.

In another exemplary embodiment, the decontamination material 30 can include sorbents such as, graphene oxide which has been shown to significantly suppress both DNA and RNA viruses due to its unique structure where sharp edges of the graphene plane were demonstrated to effectively "cut" into the cellular structure of the pathogen 64. Combinations thereof such as graphene oxide or reduced graphene oxide composited (or functionalized) with silver, copper or zinc nanoparticles can also be envisioned.

Figure 4:
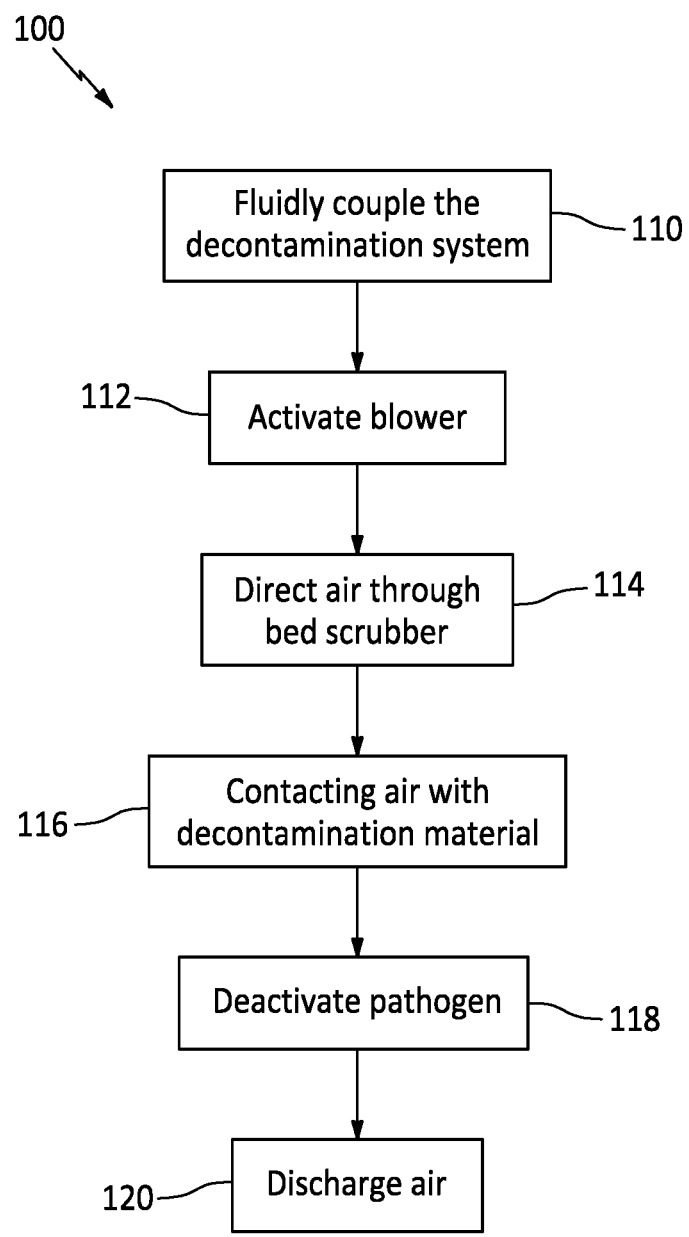
FIG. 4 is a process diagram of an exemplary decontamination process.

Referring to FIG. 4, a process diagram 100 is shown. The decontamination system 10 can be employed in a variety of locations associated with people potentially exposed to pathogens 64, such as the vehicle 24, buildings, and outdoor areas. At step 110 the decontamination system 10 is fluidly coupled to a space 62 to be decontaminated, such as the vehicle cabin 26. The inlet 40 and/or outlet 42 can be fluidly coupled with the cabin 26. Alternatively, the entire decontamination system 10 can be located within the cabin 26. In another alternative embodiment, the decontamination system 10 can be integrated into the existing vehicle interior air treatment system, such as component 22 to utilize the vehicle blower and ductwork. The component 22, can be an auxiliary air conditioning system, a cabin air heater/window defroster system and the like. At step 112, the blower 44 can be activated to flow air 38, 48 into the inlet 40. At step 114 the air is directed through the bed scrubber 28. At step 116 the air 38, 48 is contacted with the decontamination material 30. At step 118, the pathogens 64 in the air are rendered ineffective. The UV-light source 54 can irradiate portions of the decontamination material 30 to activate the photo catalysts 56. At step 120 the air is discharged through the outlet 42. It is contemplated that the air 38, 48 can be recirculated through the decontamination system 10 to ensure a safe level of pathogen 64 destruction. Recirculation ducts 66 can be provided to facilitate such recirculation as needed.

A technical advantage of the decontamination system 10 can be found in the method of delivering the air to the catalytic or active material surface of the bed scrubber 28. The substrate 32 includes the layered mesh 34 that encompasses a high reaction surface per unit volume for contact among the contaminated air 38, 48, the catalyst 56 and a photon flux 60 due to the multiple layer 33 configuration of the catalyst-coated mesh 34, a high surface area of catalyst 56 is illuminated by the photon flux 60, increasing the contact surface of the contaminated air 38 with the photocatalytic decontamination material 30. Note that at least 2 layers 33 of specifically designed MICROLITH® brand substrate mesh 34 can be required to fully adsorb all incident radiation, provided that the open area of mesh 34 is about 75-90%.

A decontamination process and system have been provided. While the decontamination process and device has been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:
1. A decontamination system comprising:
    an enclosure having sidewalls, said sidewalls defining a cavity;
    an inlet fluidly coupled to said cavity, said inlet configured to receive air into said cavity;
    an outlet fluidly coupled to said cavity, said outlet configured to discharge said air from said cavity;
    a bed scrubber located within said cavity fluidly coupled to said inlet and said outlet; said bed scrubber comprising a substrate with decontamination materials attached to said substrate;
    a blower fluidly coupled to said inlet and said outlet, said blower configured to transfer air from said inlet through said bed scrubber and out said outlet; and
    a power source electrically coupled to said substrate configured to electrically heat said substrate to a predetermined temperature configured to deactivate a pathogen.
2. The decontamination system according to claim 1, wherein said decontamination materials are configured to deactivate pathogens.
3. The decontamination system according to claim 1, wherein said decontamination materials comprise sorbent or catalyst materials functionalized with particles that have antiviral, antibacterial or antifungal properties.
4. The decontamination system according to claim 1, wherein said substrate comprises at least one of a mesh and a nano fiber support and combinations thereof.
5. The decontamination system according to claim 1, further comprising:
    at least one UV-light source configured to radiate photocatalysts coupled to said substrate.
6. The decontamination system according to claim 1, wherein said substrate comprises an ultra-short-channel-length metal substrate.
7. The decontamination system according to claim 1, wherein said decontamination materials are synthesized from graphene, graphene oxide, alumina, activated carbon or silica functionalized with particles that have antiviral, antibacterial or antifungal properties.
8. A vehicle equipped with a decontamination system comprising:
    a vehicle comprising a cabin, said cabin defining an interior and an exterior;
    an enclosure having sidewalls, said sidewalls defining a cavity;
    an inlet fluidly coupled to said cavity, said inlet configured to receive air into said cavity from at least one of said interior of said cabin and said exterior of said cabin;
    an outlet fluidly coupled to said cavity, said outlet configured to discharge said air from said cavity into said cabin;
    a bed scrubber located within said cavity fluidly coupled to said inlet and said outlet; said bed scrubber comprising a substrate with decontamination material attached to said substrate; and
    a blower fluidly coupled to said inlet and said outlet, said blower configured to transfer said air from said inlet through said bed scrubber and out said outlet; and
    a power source electrically coupled to said substrate configured to electrically heat said substrate to a predetermined temperature configured to deactivate a pathogen.
9. The vehicle equipped with a decontamination system according to claim 8, wherein said decontamination materials comprise sorbent or catalyst material functionalized with particles that have antiviral, antibacterial or antifungal properties.

10. The vehicle equipped with a decontamination system according to claim 8, wherein said substrate comprises layers of at least one of a mesh and a nano fiber support and combinations thereof.

11. The vehicle equipped with a decontamination system according to claim 8, further comprising:
   at least one UV-light source configured to radiate photo-catalysts coupled to said substrate.

12. The vehicle equipped with a decontamination system according to claim 8, wherein said substrate comprises an ultra-short-channel-length metal substrate.

13. The vehicle equipped with a decontamination system according to claim 8, wherein said decontamination materials are synthesized from graphene, graphene oxide, alumina, activated carbon or silica functionalized with particles that have antiviral, antibacterial or antifungal properties.

14. A process for decontamination of a space comprising:
   fluidly coupling a decontamination system to said space, said decontamination system comprising:
      an enclosure having sidewalls, said sidewalls defining a cavity;
      an inlet fluidly coupled to said cavity, said inlet configured to receive air into
      an outlet fluidly coupled to said cavity, said outlet configured to discharge said air from said cavity into said space;
      a bed scrubber located within said cavity fluidly coupled to said inlet and said outlet; said bed scrubber comprising a substrate with decontamination material attached to said substrate, a power source electrically coupled to said substrate configured to electrically heat said substrate to a predetermined temperature configured to deactivate a pathogen; and
      a blower fluidly coupled to said inlet and said outlet, said blower configured to transfer said air from said inlet through said bed scrubber and out said outlet into said space;
   activating said blower;
   directing said air through said bed scrubber;
   contacting said air to said decontamination material;
   deactivating a pathogen contained in said air;
   and discharging said air from said outlet into said space.

15. The process of claim 14, wherein said decontamination materials comprise sorbent or catalyst materials functionalized with particles that have antiviral, antibacterial or antifungal properties.

16. The process of claim 14, wherein said substrate comprises at least one of a mesh and a nano fiber support and combinations thereof.

17. The process of claim 14, wherein said substrate comprises an ultra-short-channel-length metal substrate.

18. The process of claim 14, further comprising: illuminating said decontamination material with at least one UV-light source configured to radiate said decontamination materials comprising photo-catalysts coupled to said substrate.

19. The process of claim 14, wherein said space is selected from the group consisting of a vehicle cabin, a ships cabin, an aircraft cabin, and personal protective equipment.

20. The process of claim 14, wherein said decontamination materials are synthesized from graphene, graphene oxide, alumina, activated carbon or silica functionalized with particles that have antiviral, antibacterial or antifungal properties.

* * * * *